(12) United States Patent
Bak et al.

(10) Patent No.: US 9,215,853 B2
(45) Date of Patent: Dec. 22, 2015

(54) *GUZMANIA* PLANT NAMED 'VARIADA'

(71) Applicants: Elly Bak, Assendelft (NL); Nicolaas Steur, Oude Niedorp (NL)

(72) Inventors: Elly Bak, Assendelft (NL); Nicolaas Steur, Oude Niedorp (NL)

(73) Assignee: CornBak B.V. (NL)

( * ) Notice: Subject to any disclaimer, the term of this patent is extended or adjusted under 35 U.S.C. 154(b) by 0 days.

(21) Appl. No.: 14/278,694

(22) Filed: May 15, 2014

(65) Prior Publication Data

US 2015/0327456 A1 Nov. 19, 2015

(51) Int. Cl.
*A01H 5/02* (2006.01)
*A01H 5/10* (2006.01)
*A01H 1/02* (2006.01)

(52) U.S. Cl.
CPC ... *A01H 5/02* (2013.01); *A01H 1/02* (2013.01)

(58) Field of Classification Search
USPC .......................................................... Plt./371
See application file for complete search history.

(56) References Cited

U.S. PATENT DOCUMENTS

PP10,575 P * 8/1998 Bak et al. ...................... Plt./371

* cited by examiner

*Primary Examiner* — David H Kruse
(74) *Attorney, Agent, or Firm* — Cassandra Bright

(57) ABSTRACT

A new and distinct *Guzmania* hybrid named 'VARIADA' characterized by solid growth habit; funnel-form rosette plant, measuring about 50 cm in height (above the pot when flowering); numerous, green colored foliage (measuring about 50 cm length and about 4.5 cm in width) Superior floral bract production; bracts are orange-red in color (closest to RHS 32A and 17A) compound inflorescence, measuring about 18 cm in height and about 20 cm in diameter; and long-lasting habit.

3 Claims, 2 Drawing Sheets
(2 of 2 Drawing Sheet(s) Filed in Color)

GUZMANIA PLANT NAMED 'VARIADA'

The present invention relates to a new, distinct and stable hybrid of *Guzmania* hybrid, hereinafter referred to as 'VARIADA'. The present invention relates to seeds which are the *Guzmania* hybrid 'VARIADA', as well as, plants and plant parts produced by these seeds which have all of the morphological and physiological characteristics of the *Guzmania* hybrid 'VARIADA'. The present invention also relates to methods for producing these seeds and plants of the *Guzmania* hybrid 'VARIADA'. Furthermore, the present invention relates to a method of producing progeny *Guzmania* plants by crossing *Guzmania* 'VARIADA', as either the female or seed or male or pollen parent, with another *Guzmania* plant and selecting progeny.

BACKGROUND OF THE INVENTION

The present invention relates to a new, distinct and stable hybrid of *Guzmania* hybrid, and hereinafter referred to by the variety denomination 'VARIADA'. The new *Guzmania* 'VARIADA' originated from a cross made in a controlled breeding program by the inventors in 2009, and then first flowered in 2012, in Assendeift, The Netherlands. The female or seed parent is the *Guzmania lingulata* inbred line identified by code 87055 (unpatented). The male or pollen parent is the *Guzmania wittmackii* inbred line identified by code 09160344 (unpatented).

*Guzmania* is a member of the Bromeliaceae family. *Guzmania* is predominantly epiphytic with a few terrestrial species and is native to the tropics. For the most part, species vary in diameter from 7 or 8 inches to 3 or 4 feet and have rosettes of glossy, smooth-edged leaves.

Floral bracts of *Guzmania* frequently have brilliant colors and may last for many months. The range of colors for *Guzmania* is generally from yellow through orange but may also include flame red and red-purple. White or yellow, tubular, three-petaled flowers may also appear on a stem or within the leaf rosette but are usually short-lived.

*Guzmania* may be advantageously grown as pot plants for greenhouse or home use. Typically, the plants are shaded from direct sunlight. During the spring to autumn period, the central vase-like part of the leaf rosette is normally filled with water.

*Guzmania* is native to tropical America. Leaves of *Guzmania* are usually formed as basal rosettes which are stiff and entire and in several vertical ranks. *Guzmania* plants have terminal spikes or panicles which are often bracted with petals united in a tube about as long as the calyx. The ovary is superior and the seeds plumose.

Asexual propagation of *Guzmania* is frequently performed by vegetative means through the use of tissue culture practices. Propagation of *Guzmania* can also be from offshoots which can be detached from the mother plant and grown in an appropriate soil or bark mixture.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl. BROMELIEN, Verlag, Paul Parey, Berlin (1986); and Rauh, Werner, BROMELIEN, Verlag Eugen Ulmer, Stuttgart (1981).

A *Guzmania* inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect their morphological and physiological characteristics.

A need exists for a greater variety of *Guzmania* cultivars with attractive ornamental features. Additionally, a need exists for additional *Guzmania* hybrid cultivars that can be easily propagated by seed. The new *Guzmania* 'VARIADA' was developed through a controlled breeding program and exhibits unique, desirable and stable characteristics.

SUMMARY OF THE INVENTION

The present invention provides *Guzmania* plant selections that are solid, medium sized, long-lasting hybrids with superior bract production and orange-red inflorescence that exhibits good keeping quality. The present invention also provides *Guzmania* plant selections with a compound inflorescence with a unique orange-red color which distinguishes the new cultivar from typical *Guzmania*.

These and other objectives have been achieved in accordance with the present invention which provides 'VARIADA' as a new *Guzmania* cultivar that is a product of a planned breeding program conducted by the inventors, Elly Bak and Nico D. M. Steur, in Assendelft, The Netherlands, in 2009. The female or seed parent is the *Guzmania* lingulata inbred line identified by code 87055 (unpatented). The male or pollen parent is the *Guzmania* wittmackii inbred line identified by code 09160344 (unpatented).

Both parental cultivars have a sufficient degree of homozygosity such that the progeny of the cross are genetypically and phenotypically uniform. The new hybrid 'VARIADA' therefore can be produced by sexual reproduction by crossing the parental inbred lines identified by the codes 87055 and 09160344 to produce a population of progeny plants, each of which has the combination of characteristics as herein disclosed for the new hybrid 'VARIADA'.

At least 2500 seeds of the *Guzmania* hybrid 'Variada' were deposited on Aug. 22, 2014, at the American Type Culture Collection (ATCC), 10801 University Blvd., Manassas, Va., a Budapest Treaty recognized depository which affords permanence of the deposit, and accorded ATCC Accession No. PTA-121510.

OBJECTS OF THE INVENTION

The present invention relates to seeds which produce *Guzmania* hybrid 'VARIADA'. The present invention also relates to *Guzmania* plants, and parts thereof, having all the physiological and morphological characteristics of *Guzmania* hybrid 'VARIADA'. The present invention relates to a plant produced from seeds which are *Guzmania* hybrid 'VARIADA'. The present invention also relates to plant parts, such as pollen, seeds or inflorescence produced by *Guzmania* hybrid 'VARIADA'.

The present invention relates to a method of producing seed which are *Guzmania* hybrid 'VARIADA', by a crossing *Guzmania* lingulata inbred line identified by code 87055 (unpatented) as the female or seed parent with *Guzmania* wittmackii inbred line identified by code 09160344 (unpatented) as the male or pollen parent. harvesting seeds produced from said cross.

The present invention also relates to a method of producing plants having all the physiological and morphological characteristics of the *Guzmania* hybrid 'VARIADA' comprising the steps of (a) crossing *Guzmania* lingulata inbred identified by code 87055 (unpatented) as a female or seed parent with

*Guzmania wittmackii* inbred line identified by code 09160344 (unpatented) as the male or pollen parent. (b) harvesting seeds produced from said cross; and (c) producing plants from said harvested seeds.

The present invention also relates to producing progeny plants from the cross of *Guzmania* hybrid 'VARIADA', as the female or male parent, with another *Guzmania* plant, and selecting progeny plants from this cross.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Guzmania* hybrid 'VARIADA' showing the colors as true as is reasonably possible with colored reproductions of this type. Colors in the photographs may differ slightly from the color values cited in the detailed botanical description which accurately describes the color of 'VARIADA'.

DETAILED BOTANICAL DESCRIPTION

Figure 1:
FIG. 1 shows a side view perspective of the primary and top bracts produced by a typical potted, flowering plant of 'VARIADA', at 13 months of age from potting size.
Figure 2:
FIG. 2 shows a close-up side view perspective of the inflorescence and top bracts produced by a typical potted, flowering plant of 'VARIADA', at 13 months of age from potting size.

The present invention was created by the inventors, Elly Bak and Nicolaas D. M. Steur in 2009, and flowered for the first time in 2012 in Assendelft, The Netherlands.

This invention is directed to *Guzmania* plant having all the morphological and physiological characteristics of the hybrid 'VARIADA' produced from seeds which are the product of the cross of the *Guzmania lingulata* inbred line identified by code 87055 (unpatented) as the female or seed parent with the *Guzmania wittmackii* inbred line identified by code 09160344 (unpatented) as the male or pollen parent. Both parents have a sufficient degree of homozygosity such that the progeny of the cross were, and continue to be, phenotypically uniform. The new hybrid 'VARIADA' can therefore be produced by sexual reproduction by crossing of the inbred selections identified by the codes 83275 and 10007207 to produce a population of progeny plants, each of which has the combination of characteristics herein disclosed for the new hybrid 'VARIADA'.

The new hybrid 'VARIADA' can also be produced by asexually reproducing progeny from the cross of the parental inbred lines identified by the codes 87055 and 09160344. Asexual reproduction of the new cultivar by vegetative means by cuttings was first performed in 2012, in Assendelft, The Netherlands. The first 'VARIADA' plants propagated through the use of such cuttings flowered in 2014, in Assendelft, The Netherlands, and have demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'VARIADA' which in combination distinguish this *Guzmania* as a new and distinct cultivar:

1. Stemless growth habit; Funnel-form rosette plant, measuring about 50 cm in height (above the pot when flowering);
2. Numerous, green color foliage (measuring about 50 cm in length and about 4.5 cm in width.
3. Superior floral bract production;
4. Bracts are orange-red in color (closest to RI-IS 32A and 17A),
5. compound inflorescence, measuring about 18 cm in height, when flowering and about 20 cm in diameter
6. Long-lasting habit.

Of the many commercial cultivars known to the present inventors, the most similar in comparison to the new *Guzmania* hybrid 'VARIADA' is the *Guzmania* cultivar 'OSTARA'. Plants of the new hybrid 'VARIADA' differ from plants of 'OSTARA' primarily in color of the inflorescence. Primary bracts of 'VARIADA' are orange-red (closest to RHS 32a and 17A). Primary bracts of *Guzmania* 'OSTARA' are red.

'VARIADA' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant.

The aforementioned photographs, together with the following observations, measurements and values describe the new *Guzmania* 'VARIADA' as grown in a greenhouse in Assendelft, The Netherlands, under conditions which closely approximate those generally used in commercial practice. Plants of 'VARIADA' were grown in a greenhouse with day temperatures ranging from 20° C. to 28° C. and night temperatures ranging from 18° C. to 23° C. No artificial lighting or photoperiodic treatments were conducted, but plants of 'VARIADA' are forced into flowering. The following fertilizer is added when growing plants of 'VARIADA': I part nitrogen, 0.6 parts phosphor, 2 parts Kalium and 0.1 parts magnesium Color references are made to the Royal Horticultural Society Colour Chart (RHS), 2001 edition, except where general colors of ordinary significance are used. Color values were taken under daylight conditions in a greenhouse in Assendelft, The Netherlands. The age of the plants of 'VARIADA' described is about 16 weeks after flowering treatment.

Classification:
Botanical: *Guzmania* sp.
Parentage:
  Female Parent: *Guzmania lingulata* inbred line identified by code 87055 (unpatented)
  Male Parent: *Guzmania wittmackii* inbred line identified by code 09160344 (unpatented)
Plant:
General Appearance and Form:
  Height: About 50 cm (when flowering)
  Width: About 60 cm
  Shape: Funnel form rosette
  Growth habit: Stemless
  Plant Vigor: Good
Flowering Season:
  A fully grown plant can flower year round, starting 16 weeks after induction of natural light or through flowering treatment. Cold Tolerance: Frost tender. Temperatures below 5° C. may damage plants.
Fragrance: None
Foliage:
Quantity: About 14 (depending on the size of the plant)
Size of Leaf:
   Length: About 50 cm
   Width: About 4.5 cm
Overall Shape: Linear lanceolate
Apex Shape: Acuminate
Base Shape: Strap-like around central axis
Margin: Entire
Texture: Smooth
Orientation: Leaf blades arch continuously from base.
Color: Leaf color can vary somewhat depending on growing conditions.
Immature and Mature:
   Upper surface: green, RHS 137A
   Under surface: green with anthocyanin stripes, closest to RHS 137A and 184A
Venation: None
Inflorescence
Borne: Erect Stalks
Shape: compound
Size:
   Length: About 18 cm in height when flowering
   Diameter: About 20 cm
Time of Bloom: A fully grown plant can produce an inflorescence containing about 70 flowers (depending on the size of the plants), and can bloom the whole year starting about 16 weeks after natural induction or through flowering treatment.
Duration of Bloom: Each flower blooms one (1) day and the total blooming of the whole inflorescence is about 6 weeks.
Petals:
  Number: 3 per flower
  Length: About 3 cm
  Width: About 0.5 cm
  Overall Shape: Ligulate
  Apex Shape: Obtuse
  Base: Fused
  Color:
    Upper and under surfaces: yellow-orange, closest to RHS 17B
Sepals:
  Number: 3 per flower
  Length: About 3 cm
  Width: About 0.5 cm
  Overall Shape: Ligulate
  Apex Shape: Acute
  Base Shape: Fused
  Color:
    Upper and under surfaces: translucent
Bracts:
Scape Bracts:
  Quantity: About 10
  Arrangement: Alternate
Size:
    Length: About 40 cm (lowest) to about 18 cm (scape bracts positioned just below the primary bracts)
    Width: About 3.5 cm to 4.5 cm
Overall Shape: Linear-lanceolate
Apex shape: Acute
Base Shape: Fused
Margin: Entire
Texture: Smooth
Upper surfaces: lower bracts are green with anthocyanin, closest to RHS 137A, changing to orange-red, closest to RHS 32B
Under surfaces: lower bract are green with anthocyanin, closes to RHS 137A and 184A
Primary Bracts:
Quantity: About 14
Arrangement: Alternate Size:
    Length: About 17 cm (lowest) to about 8 cm (primary bracts Become shorter closer to top of plant)
    Width: A bout 3.5-4 cm
Overall shape: recurved and ovate-lanceolate
Apex shape: Acute
Base shape: Fused
Margin: Entire
Texture: Smooth
Color:
    Upper and under surfaces: orange-red, RHS 32A with a yellow tip at the top primary bracts RHS 17A
Floral bracts: disposed within the inflorescence
Reproductive Organs:
Androecium:
Stamen:
  Number: 6 per flower
  Length: About 4 cm
  Diameter: About 1 mm
  Color: yellow-white, too small to distinguish RHS value
Anther:
  Length: About 0.5 cm
  Color: yellow-white, too small to distinguish RHS value
Pollen:
  Amount: none
Gynoecium:
Pistil:
  Number: I per
  flower Length:
  About 5 cm
Stigma:
  Shape: 3-parted
  Width: About 3 mm
  Color: yellow, too small to distinguish RHS value
Style:
  Length: About 4.5 cm
  Color: yellow, too small to distinguish RHS value
Ovary:
  Position: Superior
  Shape: Conical
  Length: About 0.5
  cm Diameter: About
  0.3 cm
  Color: yellow-green, closest to RHS 149D
SEEDS/FRUIT: sterile hybrid, no seed or fruit produced.
DISEASE/PEST RESISTANCE AND SUSCEPTIBILITY: Neither resistance nor susceptibility to normal diseases and pests of *Guzmania* observed.

We claim:

1. A *Guzmania* plant named 'VARIADA', representative seed deposited at the American Type Culture Collection (ATCC) having deposit Designation PTA-121510.

2. A *Guzmania* seed the deposited at the American Type Culture Collection (ATCC) having deposit Designation PTA-121510.

3. A plant part obtained from the *Guzmania* plant of claim 1.

* * * * *